United States Patent [19]

Günther et al.

[11] 4,039,531
[45] Aug. 2, 1977

[54] 4-STILBENYL-1,2,3-TRIAZOLES, PROCESS FOR PREPARING THEM AND THEIR USE AS OPTICAL BRIGHTENERS

[75] Inventors: Dieter Günther; Rüdiger Erckel, both of Kelkheim, Taunus; Erich Schinzel, Hofheim, Taunus; Günter Rösch, Altenhain, Taunus, all of Germany

[73] Assignee: Hoechst Aktiengesellschaft, Frankfurt am Main, Germany

[21] Appl. No.: 612,701

[22] Filed: Sept. 12, 1975

[51] Int. Cl.$^2$ ............................................. C07D 249/06
[52] U.S. Cl. ................................ 542/462; 252/301.22; 252/301.24; 252/301.26; 252/301.29; 252/301.32; 542/454; 542/455; 542/458; 542/402; 542/447
[58] Field of Search ....... 260/240 C, 240 CA, 240 D, 260/240.1

[56] References Cited

U.S. PATENT DOCUMENTS

| | | | |
|---|---|---|---|
| 3,732,213 | 5/1973 | Balzer et al. | 260/240 CA |
| 3,816,413 | 6/1974 | Kirchmayr | 260/240 CA |
| 3,862,179 | 1/1975 | Kabas et al. | 260/240 C |
| 3,880,841 | 4/1975 | Fleck et al. | 260/240 CA |
| 3,890,305 | 6/1975 | Weber et al. | 260/240 D |
| 3,897,421 | 7/1975 | Aebli et al. | 260/240 C |
| 3,910,895 | 10/1975 | Weber et al. | 260/240 D |

FOREIGN PATENT DOCUMENTS 2,262,340 6/1973 Germany

*Primary Examiner*—Arthur P. Demers
*Attorney, Agent, or Firm*—Connolly and Hutz

[57] ABSTRACT

Compounds of the formula (I)

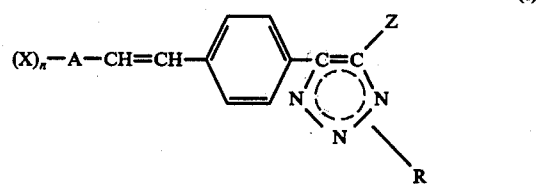

in which R is hydrogen, triphenyl-methyl or lower alkyl, which may be substituted by lower carbalkoxy, carbonamido, mono- or dialkyl carbonamido, carboxy or benzoyl, Z is cyano, carbalkoxy, carbonamido or imidazolyl, X is hydrogen, chlorine, methyl, methoxy, cyano or lower carbalkoxy, n is 1 to 3, and A is an aromatic carbocyclic group or an aromatic heterocyclic 5- or 6-membered group as well as their N-alkylated quaternary reaction products. These compounds are useful as optical brighteners and lacquers, natural or synthetic fibers and films, foils or other shaped forms made therefrom.

4 Claims, No Drawings

4-STILBENYL-1,2,3-TRIAZOLES, PROCESS FOR PREPARING THEM AND THEIR USE AS OPTICAL BRIGHTENERS

The present invention relates to 4-stilbenyl-1,2,3-triazoles, their preparation and their use as optical brighteners for natural and synthetic substrates.

In the hitherto known 4-stilbenyl-1,2,3-triazoles, the N-atom 2 always carries a group such as a phenyl, substituted phenyl or naphthyl group, or other aromatic substituents by which the conjugation is prolonged or extended (JA-OS 73/20406, German Offenlegungsschrift 2,062,383 and 2,262,340).

Now, we have found that 1,2,3-triazoles which contain, in the 4-position, an aromatic radical linked over a styryl bridge and which do not carry substituents at the ring nitrogen atoms extending the conjugation, are suitable as optical brighteners or fluorescent dyestuffs. The above-mentioned aromatic radical encompasses a continuous system of conjugated double linkages standing in conjugation with the ethylidene group to which the aromatic radical is bound.

Hence, the present invention provides compounds of the general formula (I)

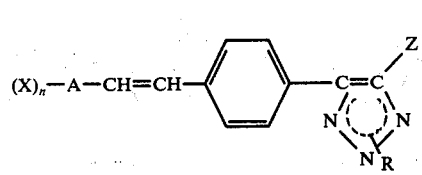

(I)

in which R represents a hydrogen atom, a triphenylmethyl group or a lower alkyl group, which may be substituted by lower carbalkoxy, carbonamido, mono- or dialkyl, carbonamido, carboxy or benzoyl groups, Z represents a cyano group or one of the groups of the formula

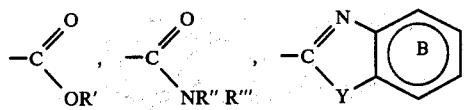

in which R', R", R''' represent a hydrogen atom, a lower alkyl group or a phenyl group, and in which the lower alkyl groups may be substituted by hydroxy, lower alkoxy, lower dialkyl amino or lower trialkyl ammonium groups and the phenyl group may be substituted by halogen atoms, lower alkyl or lower alkoxy groups, and in which R" R" and R''' together may also form a saturated bivalent radical, preferably together with the hydrogen atom to which they are bound, a pyrrolidine, piperidine, hexamethylene imine, morpholine or piperazine group, Y represents O, S or N-R$^4$ in which R$^4$ represents hydrogen or ($C_1$-$C_4$)-alkyl, in particular methyl, and the phenyl ring B may further be substituted, preferably once or twice, by ($C_1$-$C_4$)-alkyl- or -alkoxy groups or halogen atoms, in particular Cl or F, A represents an aromatic carbocyclic radical consisting of 1 to 4 annelated benzene nuclei or benzene nuclei which are linearly linked directly or over an ethylidene group, or an aromatic hetero-cyclic 5- or 6-membered radical which contains up to 3 hetero-atoms from the series of oxygen, nitrogen and sulfur atoms and which may be annelated to a benzene or naphthalene radical and/or linked over a phenylene radical, X represents hydrogen atoms or identical or different nonchromophorous radicals of the series of fluorine, chlorine or bromine atoms, lower alkyl, lower alkoxy, amino, lower mono- or di-alkyl amino, lower trialkyl ammonium, acyl amino groups, or carboxy or sulfo groups which may be functionally modified, and 2 adjacent radicals X may together also represent a lower alkylene or an 1,3-dioxapropylene group, and n represents 1 to 3.

Those compounds of the formula (I) are preferred in which R represents a hydrogen atom or a methyl or ethyl group, Z represents a cyano, carbalkoxy, carbonamido or imidazolyl group, A represents a radical of the formula

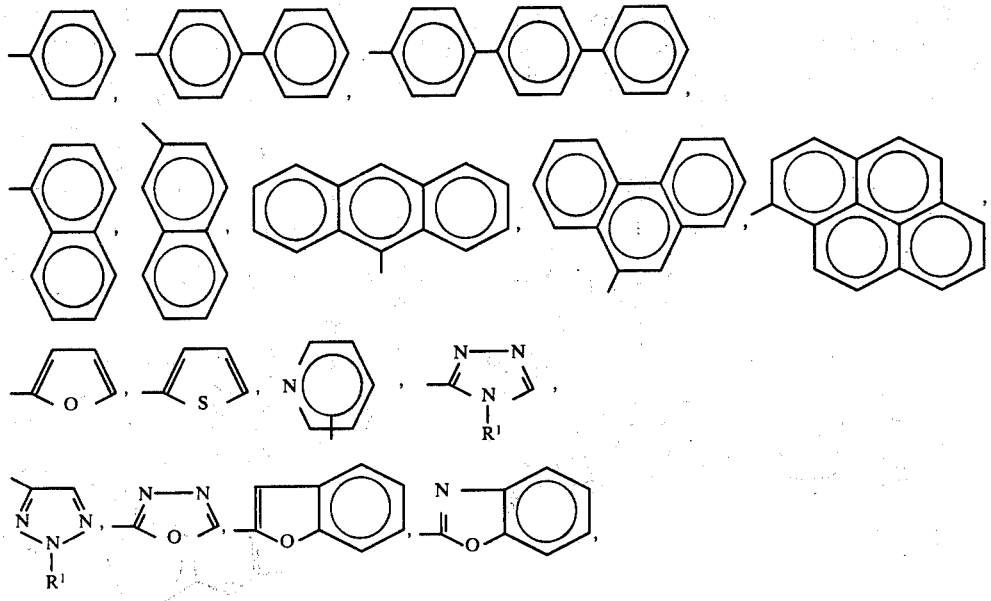

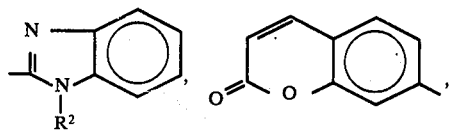

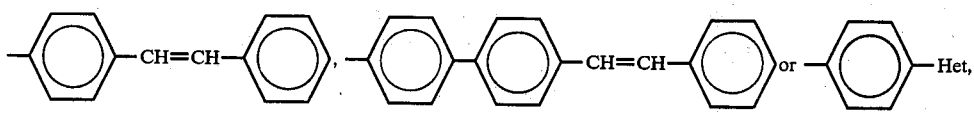

wherein Het has the following meaning:

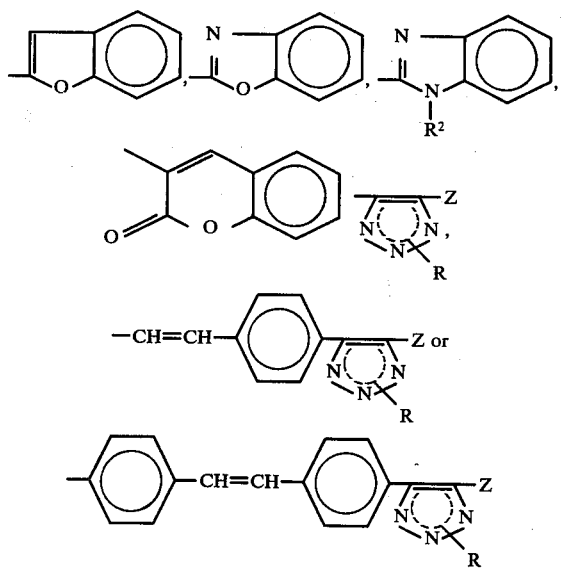

and

R[1] represents a hydrogen atom, a lower alkyl group or the phenyl group,
and

R[2] represents a hydrogen atom or a lower alkyl group.

Of particular interest are compounds of the formula (I), in which R represents a hydrogen atom or a methyl or ethyl group, Z represents a cyano, carbalkoxy, carbonamido or imidazolyl group, A represents a group of the formula

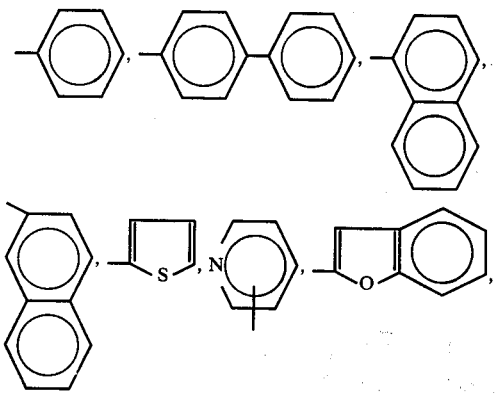

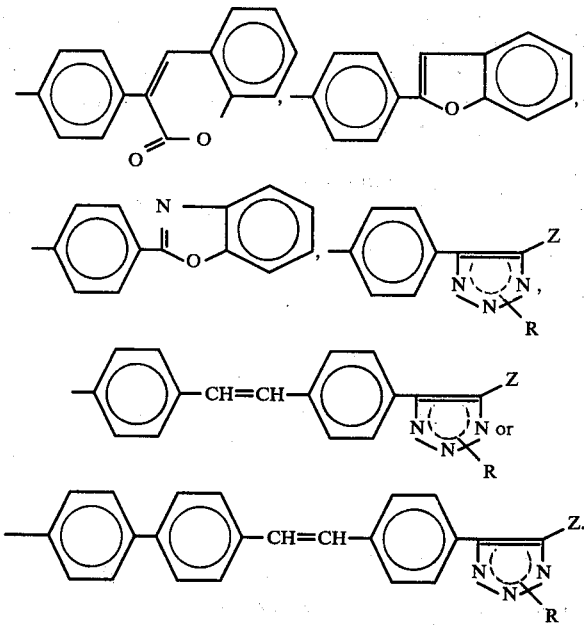

X represents hydrogen or chlorine atoms, methyl, methoxy, cyano, carboxy, lower carbalkoxy, amino, lower mono- or dialkyl-amino or lower alkanoyl-amino or benzoyl-amino groups, and $n$ is 1 to 3.

Particularly preferred as optical brighteners are the compounds of the formula (I), in which A represents a group of the formula

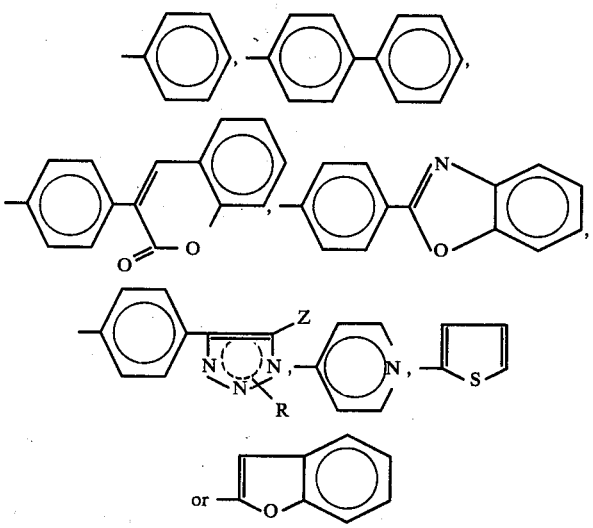

Z represents a cyano, carbalkoxy, carbonamido or imidazolyl group,

X represents hydrogen or chlorine atoms, methyl, methoxy, cyano or lower carbalkoxy groups, n is 1 to 3, and R is a hydrogen atom, a methyl or ethyl group.

If, in connection with aliphatic radicals, the term "lower" or "low molecular" is used it shall denote rests containing up to 6, preferably up to 4, and in particular up to 2, carbon atoms.

"Functionally modified" carboxy groups comprise compounds in which 1 carbon atom has 3 linkages to hetero atoms, thus in the first instances the salts, preferably the alkali metal salts, alkaline earth metal salts, the aluminium and ammonium salts, but in particular the sodium, potassium and ammonium salts of the formula

in which Y represents a lower alkyl group which may be substituted by hydroxy groups, and x represents a number from 1 to 4.

Furthermore, this term encompasses carboxylic acid esters, in particular phenyl esters and above all lower alkyl esters, the lower alkyl radicals of which may be substituted by hydroxy, lower alkoxy, lower dialkyl- amino or lower trialkyl amino groups and the phenyl group may be substituted by halogen atoms, lower alkyl or lower alkoxy groups.

"Functionally modified" carboxy groups are furthermore the acid amids and acid hydrozides, the nitrogen atoms of which may be substituted by lower alkyl groups which themselves may be substituted by hydroxy, lower alkoxy, lower dialkylamino or lower trialkyl ammonium groups, or two of such lower alkyl groups together may form a saturated bivalent group, preferably, together with the nitrogen atom to which they are bound, the pyrrolidino, piperidino, hexamethylenimino, morpholino or piperazino radical.

A "functionally modified" carboxy group is also the cyano group.

For "functionally modified" sulfo groups, the above indication shall apply in corresponding manner, i.e. with regard to the salts, esters and amides.

If the substituents mentioned under R contain phenyl rings, these phenyl rings may be substituted by 1 or 2 fluorine, chlorine or bromine atoms, lower alkyl or alkoxy groups.

It has to be understood that the groups falling under the definitions of the symbols R,Z,A,X and n may be combined one with another, but that such subgeneric language is by no means intended to introduce new matter according to 35 U.S.C. 132.

The manner in which the triazole ring in formula I is illustrated shows that the positions of the hydrogen atoms or of the alkyl groups are not determined. In general, they are mixtures of the various tautomeric or isomeric forms (T. L. Gilchrist and G. E. Gymer, Adv. Heterocycl. Chem. 16, 33 (1974); c.f. also Y. Tanaka, S. R. Velen and S. I. Miller, Tetrahedron 29, 3271 (1973) and Y. Tanaka and S. I. Miller, Tetrahedron 29, 3285 (1973)).

The compounds of the formula (I) are prepared by the addition of sodium azide on arylsulfonylethylidene compounds (Chem. Ber. 106 (1973) 2758; German Offenlegungsschrift 2.138.522). This process is characterized by that, as the arylsulfonyl compounds, a compound of the formula (II)

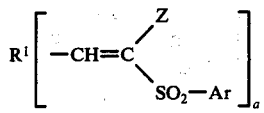

is reacted with a mole sodium azide, a being 1 or 2 and correspondingly R¹ being

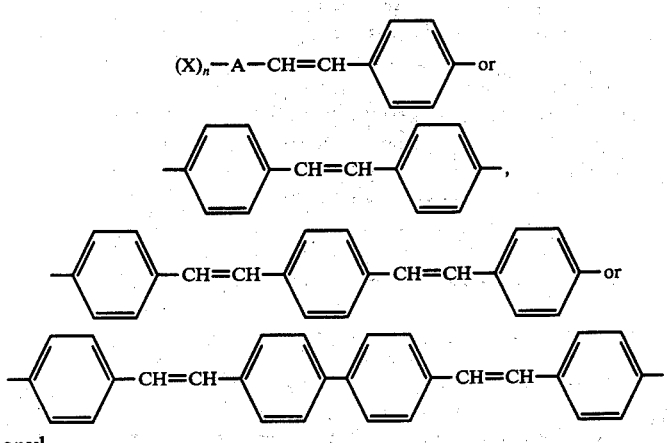

Z has the meaning given above and Ar represents a phenyl group which may be substituted by fluorine, chlorine or bromine atoms, lower alkyl, lower alkoxy, nitro or lower alkanoylamino groups, or a compound of the formula (III)

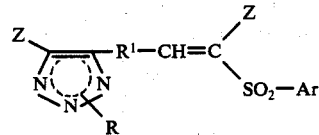

is reacted with 1 mole of sodium azide and the compounds of the formula (I) so obtained in which R represents a hydrogen atom are reacted if desired, in known manner with such organic halides or sulfates which contain the radical R.

It has proved advantageous to carry out the alkylation of the corresponding sodium salt present in dissolved form without isolation of the triazole under addition of an alkylating agent such as dialkyl sulfate or alkyl halide, at temperatures in the range of between 0° C and the boiling point of the solvent used preferably at 20° to 60° C.

The reaction of the compounds of the formula (II) or (III) with sodium azide is carried out in polar solvents, preferably dimethyl sulfoxyde, lower alkanols, acetonitrile, hexamethylphosphoric acid trisamide and in particular dimethylformamide at temperatures in the range of from 0° to 200° C, preferably 20° to 155° C, in particular 60° to 100° C.1 to about 1.2 mole of sodium azide are used for each sulfonyl group.

The pre-products of the formulae (II) and (III) can be obtained according to known methods in the following ways:

1. Compounds of the formula (II) and correspondingly also those of the formula (III) may be prepared as follows:

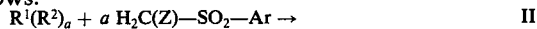
R¹(R²)ₐ + a H₂C(Z)—SO₂—Ar →  II

In the above formulae, R¹, a and Ar have the above meaning and R² represents a formyl group (condensation according to KNOEVENAGEL) or a group of the formula

—CH=NR³

(condensation according to German Auslegeschrift 1,768,868), in which R³ represents an organic radical which is bound to the nitrogen atom over a tert. carbon atom. With a view to the resulting product of the formula (II) and the final product of the formula (I), this radical is not critical and it is suitable to select a tert. butyl or a chlorophenyl group, in particular the phenyl group, for this purpose. The condensation according to KNOEVENAGEL is effected in a solvent serving as "water-dragger" (a solvent with forms with water and azeotrope which is easily decomposable), preferably an aromatic hydrocarbon, in particular benzene, toluene, or xylene or in mixtures of such solvents, if necessary with the addition of polar solvents such as dimethyl formamide or dimethyl sulfoxide as solubilizers. In general, stoichiometrical quantities of the reactants are used, if necessary an excess of aldehyde may be used. The reaction is carried out in general at normal pressure in the boiling solvent, thus at about 80° to about 150° C with addition of catalytical amounts of piperidine or a piperidine salt, for example the acetate or a mixture of piperidine or acetic ester, or also ammonium acetate. 2. By the reaction of compounds of the formula (IV)

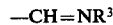
(X)ₙ—A—CH=PR₃⁴    (IV)

in which X, n and A have the meanings given above and R⁴ represents a cyclohexyl, preferably a phenyl radical, according to Wittig with a molar excess of terephthal dialdehyde to compounds of the formula

(X)ₙ—A—CH=CH—⟨phenyl⟩—CHO which are then reacted with compounds of the formula

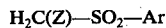
H₂C(Z)—SO₂—Ar according to the above described variant 1. It is suitable to use in this process 2 to 10, preferably 4 to 6 moles, of terephthal dialdehyde per mole of ylide. In this process the filtrate may be used again as solvent after having separated by suction filtration the product. For the following reaction, it is sufficient to use a quantity of aldehyde which is equimolar to the ylide.

The product which has been filtered off with suction consists of the corresponding trans-stilbene and has a good purity. If desired, it can be further purified by recrystallisation or similar other measures.

This process can be repeated several times, for example up to 15 times, advantageously up to 10 times, preferably up to 5 times. After removal of the solvent by distillation up to dryness, the excess terephthal-dialdehyde can be separated by dissolution from the residue with the aid of hot water or better with warm bisulfite solution and recovered of the bisulfite compound. From the remaining residue the corresponding cis-stilbene can be isolated by extraction with a suitable solvent, for example alcohols, aromatic hydrocarbons, ether, and than rearranged for example with the aid of catalytical amounts of iodine, by heating in nitrobenzene to the trans-stilbene compounds (P. Ruggeli, A. Staub, Helv. 20, (1937),37). 3. Another method consists in reacting compounds of the formula

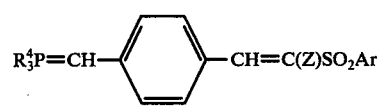
R₃⁴P=CH—⟨phenyl⟩—CH=C(Z)SO₂Ar    (V)

with aldehydes of the formula (VI)

(X)ₙ—A—CHO    (VI)

according to Wittig, in which formulae Ar, X, A and n have the meanings given above and R⁴ represents a cyclohexyl or, preferably a phenyl radical. This is also true in analogous manner for the dialdehydes of the formulae

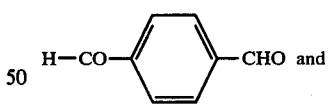
H—CO—⟨phenyl⟩—CHO and

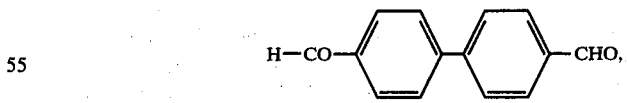
H—CO—⟨biphenyl⟩—CHO, which may be reacted with 2 mols of ylide (V).

The compounds of the formula (V) may be obtained according to the following reaction scheme:

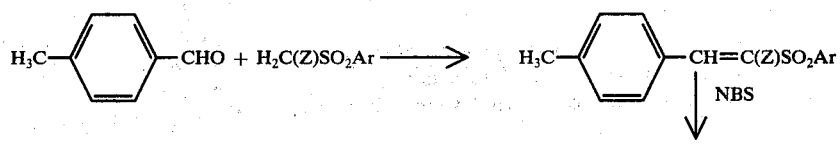
H₃C—⟨phenyl⟩—CHO + H₂C(Z)SO₂Ar ⟶ H₃C—⟨phenyl⟩—CH=C(Z)SO₂Ar
↓ NBS

-continued

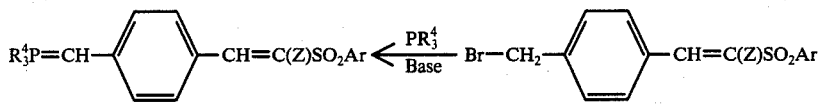

In this formulae, Ar and $R^4$ have the meanings given above, NSB denotes N-bromosuccinimide.

This reaction is suitably carried out as follows:

The bromomethyl compound is dissolved or suspended in a diluting agent such as chloroform or benzene, the phosphine $PR_3^4$ is added and the salt so obtained is reacted in a polar solvent such as dimethyl formamide, dimethyl sulfoxide or hexamethylene phosphoric/acid tris-amide with a suitable base such as a lower alkali metal alkanolate, under the protection of an inert gas to yield the ylide. The aldehyde which may be dissolved in a polar solvent is then introduced in the ylide solution or suspension so obtained and the Wittig olefination is carried out at temperatures of about 60° to about 155° C. 4. If the arylsulfonyl compounds of the formula (II) correspond to the following formula

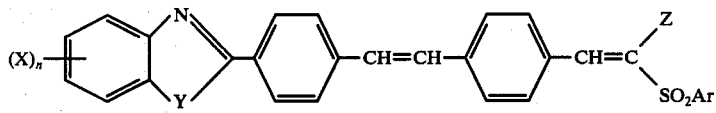

in which X represents hydrogen, fluorine, chlorine or bromine atoms, lower alkoxy, carboxy or sulfo groups which may be modified functionally, or lower alkyl, and in which the alkyl groups are subject to the proviso that they must not stand in the paraposition to heteroatoms, n represents number 1 to 3, Y represents O, S or $NR^4$, $R^4$ represents hydrogen or $(C_1-C_4)$-alkyl, in particular methyl, these compounds may also be obtained by the reaction of compounds of the general formula (VII)

(VII)

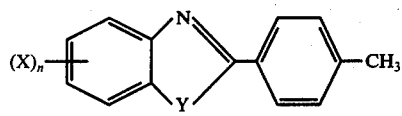

with compounds of the general formula (VIII)

(VIII)

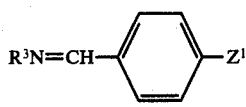

suitably in equivalent amounts, with an excess of a strong basic alkali metal compound in a polar aprotic solvent at temperatures between +10° C and 150° C, preferably between 20° C and 110° C. In this manner, compounds of the formula (IX)

are obtained.

$R^3$ in formula (VIII) represents a hydrocarbon radical which is bound to the nitrogen atom over a tert. carbon atom. Since, however, $R^3$ is eliminated in the course of these reactions and thus no longer appear in the following products, this radical is not critical and it is suitable to select a tert. butyl group or a chlorophenyl group, in particular the phenyl group.

$Z^1$ represents a cyano group or a carboxylic acid ester group, in particular a phenyl group and above all, a lower alkyl ester group.

The compounds of the formulae (VII) and (VIII) may be prepared, for example according to the process described in German Auslegeschrift 1,594,834. A solvents, there may be used in particular amides of a $(C_1-C_4)$-carboxylic acid or of phosphoric acid, which are peralkylated by lower (i.e. containing 1 to 4 carbon atoms) alkyl groups, in particular methyl groups, such as dimethyl formamide, diethyl formamide, di-methyl acetamide and hexamethyl phosphoric acid triamide. As bases, there are suitably used the hydroxides, alcoholates, amides or alkali metals or of ammonium. It is preferred to use the 4- to 8-fold quantity, referred to the compounds of the formulae (VII) or (VIII). Working in anhydrous media under inert gas with potassium alcoholates proved particularly advantageous. The reaction time may be between ½ and 3 hours. The final substances can be worked up from the reaction mixture according to the conventional known method.

If in formula (VIII) $Z^1$ represents a carboxylic acid ester grouping, it has proved advantageous for working-up to adjust the reaction mixture with a strong mineral acid, preferably concentrate hydrochloric acid, to pH = 1 and to hydrolyse the compound (IX) at boiling temperature to the free acid. It is of advantage to use an excess of mineral acid, calculated on the base used and on the ester function. The salts formed may be filtered off in the heat, provided they are insoluble in the solvents used. From the filtrate, the desired products may be filtered off by suction in the cold, optionally after addition of a diluting agent, for example acetonitrile, methanol, ethanol, water or mixtures of these aforementioned diluents, in a form which is sufficiently pure for further actions. If in formula (VIII) $Z^1$ represents the cyano group this letter may be likewise be saponified to the acid according to known methods.

(IX)

From the compounds of the formula (IX) so obtained, in which $Z^1$ represents a carboxylic acid group, the compounds of the general formula (XII)

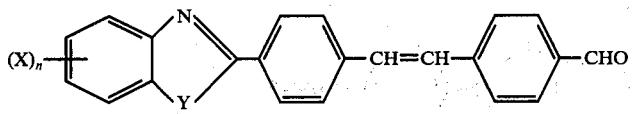

(XII)

in which X and n have the meanings given above, can be easily prepared via the acid chlorides by reduction according to Rosenmund on a poisoned palladium catalyst.

The aldehyde so formed is then suitably condensed without further isolation, after separation by filtration of the catalyst in the heat, with the compound of the formula $H_2C(Z)—SO_2Ar$ in which Z and Ar have the meanings given above, according to KNOEVENAGEL in the manner already described, and the resulting compounds are then reacted in the manner described with sodium azide, if desired with following alkylation, to yield the products of the formula (I) or (II).

The 4-stilbenyl-1,2,3-triazoles of the formula (I) show in solid and dissolved state a strong and in many cases a very distinct reddish blue fluorescence. The new compounds may be used as optical brighteners in particular in admixture with other products which show for example a greenish blue fluorescence.

The absorption may be shifted to longer wave lengths by suitable substituents in the stilbene portion of the compounds of the formula (I), for example with $(X)_nA$ = 2-methoxy-naphth-1-yl
4-methoxy-naphth-1-yl
4-N,N-dimethylaminophenol
4'-(5-cyano-1,2,3,-[H]-triazole-4-yl)-stilbene-4-yl
4'-[4'-(5-cyano-1,2,3-[H]-triazole-4-yl)-stilbene-4-yl]-phenyl, in such a manner that dyestuffs showing a greenish yellow fluorescence are obtained. Also with these products the alkylation of the triazole rings is possible in order to vary the optical and other properties required for utilization.

As optical brighteners, in particular the following new compounds of the formula (I) are suitable:
a. 4-(4'-benzoxazole-2-yl-stilbene-4-yl)-5-carbonamido-1,2,3-triazole
b. 4-(4'-benzoxazole-2-yl-stilbene-4-yl)-5-benzoxazole-2-yl-1,2,3-triazole In the same manner there are suitable as optical brighteners the N-methyl compounds of the formula (I), which are obtained, for example by the reaction of the products with dimethyl sulfate, as well as the corresponding N-ethyl compounds obtained, for example by reaction with diethylsulfate.

The reaction products obtained by these alkylations constitute mixtures of the 3 possible isomers the chromatographic separation of which is possible (for example on silica gel with benzene or chloroform), but which is not necessary because the isomer mixtures may be used in the same manner as optical brighteners as the pure components.

As substrates to be brightened, there may be mentioned, for example the following materials: lacquers, natural and synthetic fibers, for example those made of natural or regenerated cellulose acetyl cellulose, natural and synthetic polyamides, such as wool, polyamide-6 and -6.6, polyesters, polyolefines, polyvinylchloride, polyvinylidene chloride, polystyrene or polyacrylonitrile, as well as foils, films, ribbons or bands or shaped bodies made of such materials.

The compounds of the invention which are insoluble in water may be used in the form of solutions in organic solvents or in the form of aqueous dispersions prepared advantageously with the aid of a dispersing agent. As dispersing agents there may be used, for example soaps, polyglycol ethers, which derive from fat alcohols, fatty amines or alkyl phenols, cellulose sulfite waste lyes or condensation products of naphthalene-sulfonic acid with formaldehyde which may be alkylated.

The compounds of the general formula (I) may also be added to detergents. These latter may contain the usual fillers and axiliary substances such as alkali metal silicates, alkali metal phosphates and -polymetaphosphates, alkali metal borates, alkali metal salts of carboxy-methyl celluloses, foam stabilizers such as alkanol amides of higher fatty acids or complex formers such as soluble salts of ethylene-diamine-tetraacetic acid or diethylene triaminepentaacetic acid, as well as chemical regent agents such as perborates or percarbonates.

Brightening of the fibres materials with the aqueous or optionally organic brighteners is carried out either according to the exhaust process at temperatures in the range of, preferably, about 20° to about 150° C, or under the conditions of the thermosol process, in which the textile material is impregnated or sprayed with the solution or dispersion of the optical brightener and squeezed between rollers to a residual moisture content of about 50 to about 120%. The textile material is then subjected for about 10 to about 300 sec. to a heat treatment, preferably with the aid of dry heat, at about 120° to about 240° C. This thermosol process may also be combined with other finishing operations, for example with a finishing process in order to improve the easycare properties.

Furthermore the compounds of the invention may be added to high molecular organic materials before or during their shaping. Thus for example they may be added in the preparation of films, foils, bands or ribbons or shape bodies to the press masses or be dissolved in the spinning maass prior to spinning. Suitable compounds may also be added to low molecular starting materials prior to the polycondensation or polymerisation, as in the case of polyamide-6, polyamide-6.6 or linear esters of the type of the polyethyleneglycol terephthalate.

Compounds of the invention which are substituted by one or, preferably, 2 carboxy or carbalkoxy groups, may be bound to linear polyester molecules and synthetic polyamides by an ester or amide linkage, if they are added to these materials or preferably to the starting materials thereof, under suitable conditions. Optical brighteners fixed in this manner by a chemical linkage to the substrate are distinguished by an extra-ordinarily high fastness to sublimation and to solvents.

The quantity of the compounds of the general formula (I) to be used according to the invention, referred to the material to be optically brightened, may vary within wide limits depending on the field of applications and on the effect desired. It can easily be determined by preliminary tests and is in general between about 0.01 and about 2%.

The following examples illustrate the invention.

EXAMPLE 1

2-[4-(4'-benzoxazole-2-stilbene-4-yl)-5-cyano-1,2,3-triazole-N-yl]-methylacetate 3.9 g (10 mmoles) of 4-(4'-benzoxazole-2-yl-stilbene-4-yl)-5-cyano-1,2,3-(H)-triazole, and 1.9 g (10 mmoles) of tris-iso-propanolamine were dissolved in 250 ml of absolute DMF under an atmosphere of nitrogen, combined with 2.2 g (20 mmoles) of chloroformic acid methyl ester and stirred for 4 hours at 100° C. After cooling, 600 ml of ice-water were added, the whole was acidified with 2N-acetic acid, filtered with suction, washed with methanol and dried.

3.9 g (85% of the theory) of a odorless powder of 2-[4-(4'-benzoxazole-2-yl-stilbene-4-yl)-5-cyano-1,2,3-triazole-N-yl[-acetic acid methyl ester was obtained; after two recrystallization from dioxane/bleaching earth, the product had a melting point of 248° -249° C.

Absorption-
$\lambda$ max = 363 nm
$\epsilon$ = 7.14 × 10$^4$

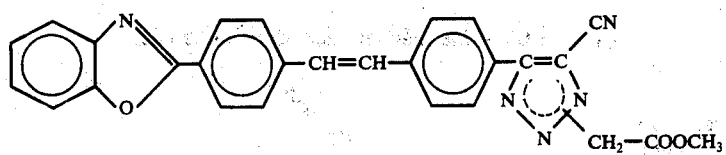

The starting compound 4-(4'-benzoxazole-2-yl-stilbene-4-yl)-5-cyano-1,2,3-(H)-triazole was prepared by reacting p-methylbenzaldehyde with phenylsulfonyl-acetonitrile, brominating the resulting 1-p-tolyl-2-cyano-2-phenylsulfonyl-ethylene with N-bromosuccinimide to 1-(4-bromomethyl-phenyl)-2-cyano-2-phenyl-sulfonyl-ethylene, which is then reacted with triphenyl-phosphine to give the corresponding phosphonium salt. This is reacted in dimethylformamide with p-formyl-phenyl-2-benzoxazole to give 1-(4'-benzoxazole-2-yl-stilbene-4-yl)-2-cyano-2-phenylsulfonylethylene which in turn upon heating in dimethylformamide with sodium azide gives the 4-(4'-benzoxazole-2-yl-stilbene-4-yl)-5-cyano-1,2,3-(H)-triazole.

The compounds indicated in Table I were prepared in analogous manner.

Table I

| R | Fp. (° C) | Yield % | Absorption in DMF max (nm) |
| --- | --- | --- | --- |
| —C(C$_6$H$_5$)$_3$ | 248–249 | 64,8 | 365 |
| —CH$_2$—CONH$_2$ | 300 | 62,7 | 363 |
| —CH$_2$—COOH | 299–300 | 55,9 | 364 |
| —CH$_2$—C(=O)—C$_6$H$_5$ | 263–264 | 67,8 | 363 |

EXAMPLE 2

4-(4'-benzoxazole-2-yl-stilbene-4-yl)-5-cyano-N-acetamide-1,2,3-triazole 4.9 g (10 mmoles) of 1(4'-benzoxazole-1-yl-stilbene-4-yl)-2-cyano-2-phenylsulfonyl-ethylene were suspended in 80 ml of absolute dimethylformamide under an atmosphere of hydrogen and combined at 40° C with 0.78 g (12 mmoles) of sodium azide. The mixture was stirred for 5 hours at 100° C, cooled at 60° C, combined with 1 g (11 mmoles) of chloracetamide in 20 ml of DMF and stirred for 5 hours at 60° C. After cooling to room temperature the mixture was combined with 200 ml of methanol, filtered with suction and the product was washed with water and methanol. After drying, 2.8 g of 4-(4'-benzoxazole-2-yl-stilbene-4-yl)-5-cyano-N-acetamide 1,2,3-triazole were obtained which, after recrystallization from dimethylformamide, had a melting point of 300° C.

Absorption:
$\lambda_{max}$ = 363 nm
$\epsilon$ = 7.11 × 10$^4$

EXAMPLE 3 a. 2-(p-bromomethyl)-phenyl-benzoxazole 21 g (0.1 mole) of 2-p-tolyl-benzoxazole were dissolved in 200 ml of chlorobenzene. The reaction mixture was heated to reflux, the reaction vessel was irradiated with a 500 watt lamp and a solution of 5.2 ml (0.2 mole) of bromine, dissolved in 80 ml of chloro-benzene, was added dropwise. The speed of the dropwise addition was regulated in such a manner that no bromine vapours developed within the reaction vessel. After 4 horus the whole amount had been dropwise added. The reaction mixture was stirred for 1½ hours and filtered with suction while ice cooled. After drying, 17.3 g (60%) of 2-(p-bromomethyl)phenylbenzoxazole melting at 164 to 165° C were obtained.

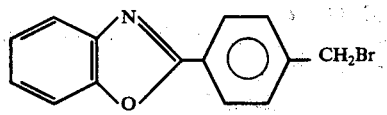

b. 2-(4-triphenylphosphoniummethylene-phenyl)-benzoxazole-bromide 17.3 g (60 mmoles) of 2-p-bromomethyl-phenyl-benzoxazole were combined with 100 ml of triphenylphosphine, dissolved in 35 ml of benzene. The reaction mixture was stirred for 24 hours at room temperature and for 8 hours at 50° C, filtered with suction at room temperature, and the resulting product was washed with benzene and dried, 28 g (85% of the theory) of 2-(4-triphenylphosphoniummethylene-phenyl)-benzoxazole bromide were obtained.

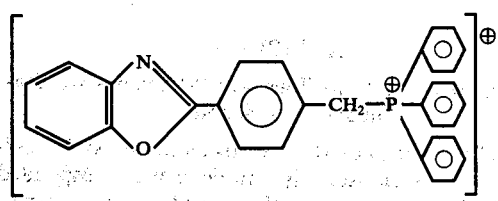

c. 4-(4'-benzoxazole-2-yl)-stilbene-aldehyde 77 g (140 mmoles) of 2-(4-triphenylphosphoniummethylenephenyl)-benzoxazole-bromide and 94 g (700 mmoles) of terephthalaldehyde were dissolved in 1800 ml of absolute DMF under an atmosphere of nitrogen and heated up. 15.7 g (140 mmoles) of potassium-tert.-butylate were added portionwise at an ineral temperature of 40° C. The reaction mixture was then heated to 100° C and stirred for 5 hours at this temperature. 1200 ml of DMF were removed by destillation and the residue was filtered with suction at 0° C. The filter residue was stirred with 400 ml of hot water, filtered with suction, washed with methanol and dryed. 23 g (50.6% of the theory) of crude 4-(4'-benzoxazole-2-yl)-trans-stilbene-aldehyde were obtained. After recrystallization from toluene with bleaching earth yellow cristals melting at 228° to 230° C were obtained.

IR: $-C\overset{O}{\diagdown}$  1710 cm$^{-1}$  UV: $\lambda_{max}$[nm] = 364  $\epsilon$ = 5,82 × 10$^4$ The filtrate obtained from the DMF-solution was evaporated to dryness in a rotary evaporator and the residue was stirred for 1 hour at 80° C with 400 ml of water and 80 ml of a bisulfite solution and finally filtered with suction. After decomposition of the bisulfite compound with 2 N-sodium hydroxide solution the terephthal aldehyde used in excess separates in the filtrate. After suction filtration, washing with water and drying, 57 g of terephthal aldehyde melting at 112° to 114° C were obtained.

After two recristallizations from ethanol/charcoal there were obtained from the residue 8 g (18%) of 4-(4'-benzoxazole-2-yl)cis-stilbene-aldehyde melting at 116° to 117° C.

IR: $-C\overset{O}{\diagdown}$  1710 cm$^{-1}$  UV: $\lambda_{max}$[nm] = 346  $\epsilon$ = 3,2× 10$^4$ The cis-compound could be rearranged by heating with nitrobenzene and 1% by weight of iodine as catalyst into the corresponding trans-compound.

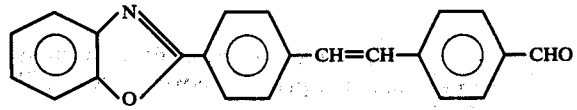

d. 2-(phenylsulfonyl)-methyl-benzoxazole 33 g (0.2 mole) of 2-chloromethylbenzoxazole and 32.8 g of sodium benzene sulfonate were dissolved in 200 ml of DMF, heated within one-half hour to 70° C, for 1 hour at 70° C, for 1 hour to 80° C and for 1 hour to 90° C, and after cooling, allowed to flow into 300 ml of H$_2$O, while stirring well. The reaction mixture was filtered with suction, washed well with H$_2$O and dried. 48.8 g (98.4% of the theory) were obtained. After recristallization from ethanol, 41 g of colorless cristals melting at 108° to 109° C were obtained.

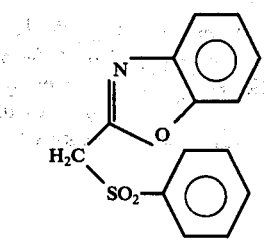

In the same manner there were obtained:

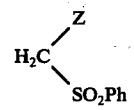

| Z | Mp/Bp (° C) | yield (% d.Th.) | NMR $C\overset{H}{\diagdown}_H$ (ppm) |
|---|---|---|---|
| —COOCH$_3$ | BP$_{0,01}$: 160 | 79 | 4,15 |
| —COOC$_2$H$_5$ | BP$_{0,01}$: 150 | 83 | 4,1 |
| —CONH$_2$ | 147–148 | 64 | 4,56 |
|  | 215 | 68 | 4,4 |

-continued

| Z | Mp/Bp (°C) | yield (% d.Th.) | NMR C⟨H,H (ppm) |
|---|---|---|---|
| 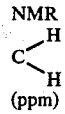 —⟨phenyl⟩—COOCH₃ | 168–169 | 63 | 4,7 |
| 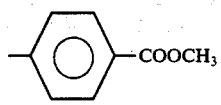 benzimidazolyl | 209–210 | 75 | 4,98 | e. 1-(4'-benzoxazole-2-yl-stilbene-4-yl)-2-benzoxazole-2-yl-2-phenylsulfonyl-ethylene 16.5 g (50 mmoles) of 4-(4'-benzoxazole-2-yl)-stilbenealdehyde and 14 g (50 mmoles) of 2-(phenyl-sulfonyl)-methylbenzoxazole were boiled in 300 ml of toluene with 1 ml of piperidine and 0.5 ml of glacial acetic acid for 1½ hours on a water separator. After suction-filtration at room temperature, washing with methanol and drying, 25 g (86% of the theory) of 1-(4'-benzoxazole-2-yl-stilbene-4-yl)-2-benzoxazole-2-yl-2-phenylsulfonyl-ethylene in the form a yellow powder melting at 280° to 281° C were obtained.

f. 4-(4'-benzoxazole-2-yl-stilbene-4-yl)-5-benzoxazole-2-yl-1,2,3-[H]-triazole 11.6 g (20 mmoles) of 1-(4'-benzoxazole-2-yl-stilbene-4-yl)-2-benzoxazole-2-yl-2-phenylsulfonyl-ethylene were suspended in 150 ml of absolute DMF under an atmosphere of nitrogen and combined at 40° C, portionwise, with 1.6 g (24 mmoles) of sodium azide. The whole was stirred for 3 hours at 100° C, and after cooling allowed to run into 400 ml of water and acidified with 2 N-acetic acid. The residue was filtered off with suction, dried and boiled in 100 ml of o-dichlorobenzene for one-half hour under reflux. After cooling, the product was filtered off with suction, washed with methanol UV: λ$_{max}$[nm] = 383   ε = 6,3 × 10⁴

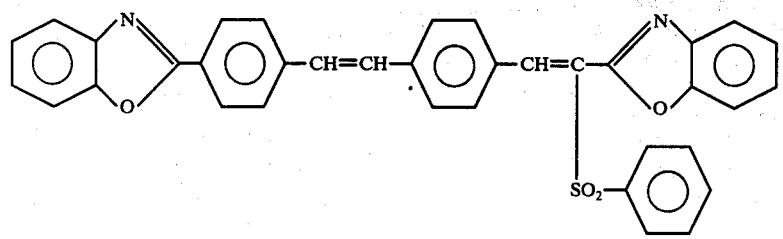

In the same manner there were obtained:

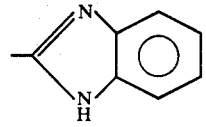

| Z | Mp. (°C) | yield % | Absorption in DMF λmax [nm] | coeff. ε × 10⁻⁴ |
|---|---|---|---|---|
| —COOCH₃ | 205–206 | 69 | 363 | 5,57 |
| —COOC₂H₅ | 230–231 | 56,5 | 377 | 6,74 |
| —CONH₂ | 278–280 | 94,7 | 374 | 7,60 |
| benzimidazolyl | 285–286 | 87,3 | 380 | 6,58 | and dried. 9 g (94% of the theory) of 4-(4'-benzoxazole-2-yl-stilbene-4-yl)-5-benzoxazole-2-yl-1,2,3-[H]trizole melting at 300° C were obtained.

IR: νNH 3300 cm⁻¹,   MS: M+/e 481,   UV (in DMF): λ$_{max}$ = 368 nm   ε = 4,42 × 10⁴

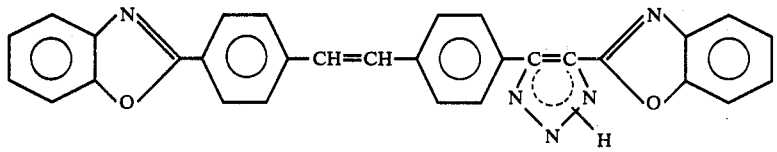

In the same manner there were prepared:

| Z | Mp. (°C) | yield % | Absorption in DMF λmax [nm] |
|---|---|---|---|
| —COOCH₃ | 246–247 | 86,6 | 363 |
| —COOC₂H₅ | 250–251 | 80,0 | 363 |
| —CONH₂ | >300 | 82,3 | 366 |
| (benzimidazolyl) | >300 | 98 | 367 | g. 4-(4'-benzoxazole-2-yl-stilbene-4-yl)-5-benzoxazole-2-yl-N-methyl-1,2,3-triazole 2.5 g (5 mmoles) of 4-(4'-benzoxazole-2-yl-stilbene-4-yl)-5-benzoxazole-2-yl-1,2,3-[H]-triazole were stirred with 1.3 g (12 mmoles) of anhydrous potassium carbonate and 0.76 g of dimethylsulfate in 30 ml of absolute DMF for 8 hours at 60° C, the solution was filtered off with suction while ice-cooled and the residue was isolated by stirring twice with each time 100 ml of water having a temperature of 60° C. After filtration with suction, washing with methanol and drying, 2.3 g (92.8% of the theory) of 4-(4'-benzoxazole-2-yl-stilbene-4-yl)-5-benzoxazole2-yl-N-methyl-1,2,3-triazole were obtained which, after two recristallizations from a mixture of DMF/bleaching earth showed a melting point of 246° to 249° C.

Absorption:

$\lambda_{max} = 363$ nm $\epsilon = 6,3 \times 10^4$

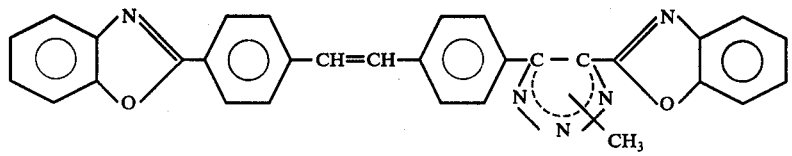

In a manner analogous to that described above the following compounds indicated in table II were obtained.

Table II

| Z | R | Mp. (°C) | yield % | Absorption in DMF λmax [nm] |
|---|---|---|---|---|
| —COOCH₃ | —CH₃ | 198–199 | 75,6 | 359 |
| —COOC₂H₅ | —C₂H₅ | 258–259 | 53,2 | 360 |
| —CONH₂ | —C₂H₅ | 270–271 | 67,4 | 363 |
| —CONH₂ | —CH₃ | 297–298 | 58,2 | 363 |
| (benzoxazolyl) | —CH₃ | >300 | 60,5 | 353 |
| (benzoxazolyl) | —C₂H₅ | 254–255 | 75,1 | 363 |

Table II-continued
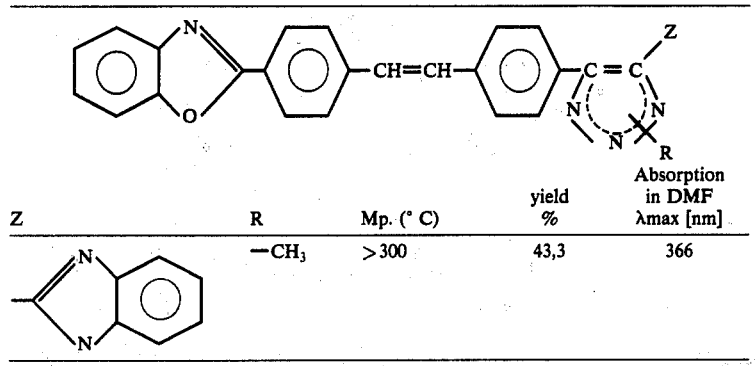
| Z | R | Mp. (° C) | yield % | Absorption in DMF λmax [nm] |
|---|---|---|---|---|
| 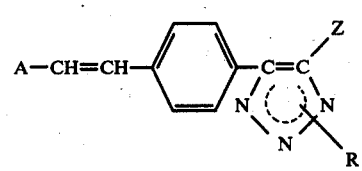 | —CH₃ | >300 | 43,3 | 366 |
We claim:
1. A compound of the formula (I)
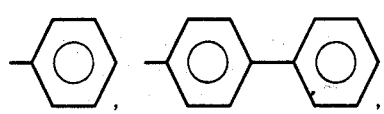
wherein
R is hydrogen, methyl or ethyl, R being other than hydrogen when Z is cyano,
Z is cyano, carbalkoxy, carbonamido or imidazolyl,
A is a group of the formula
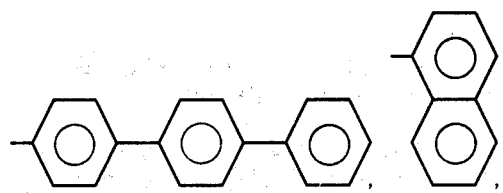
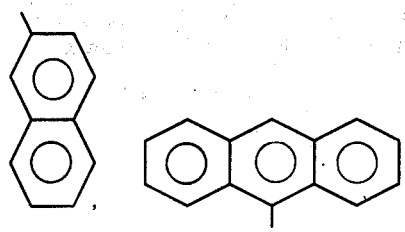
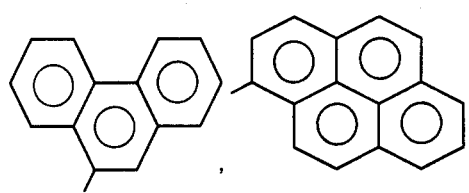
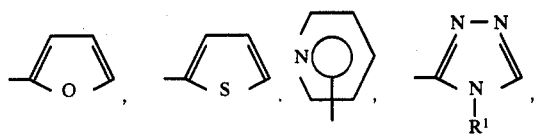
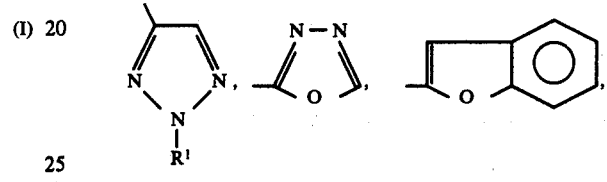
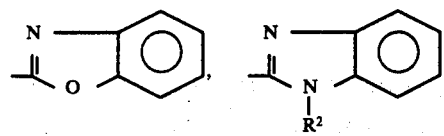
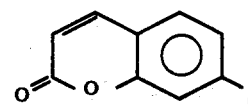
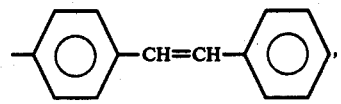
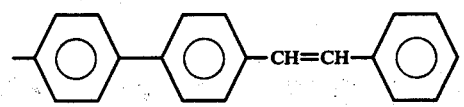
wherein Het has the following meaning:
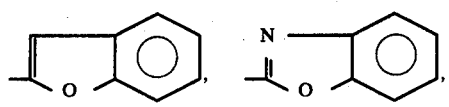
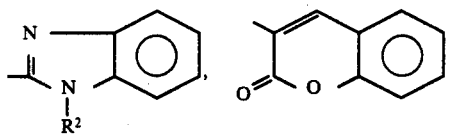
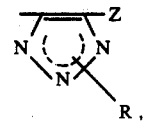

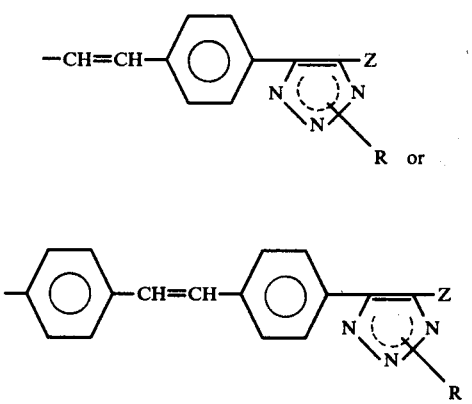

and

R[1] is hydrogen, lower alkyl or phenyl, and

R[2] is hydrogen or lower alkyl.

2. A compound as claimed in claim 1, wherein A is a group of the formula

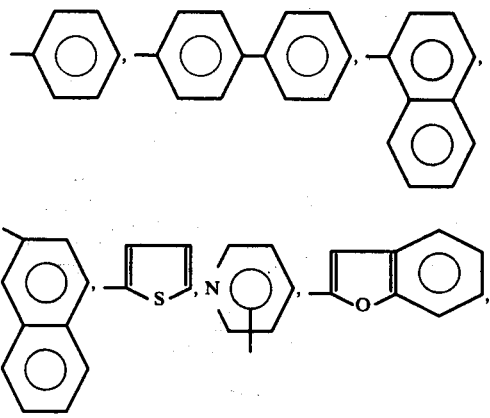

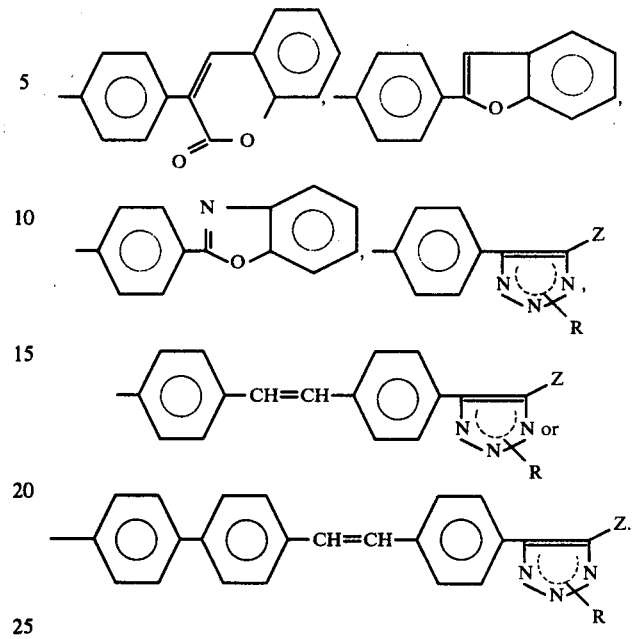

3. A compound as claimed in claim 1 wherein A is a group of the formula

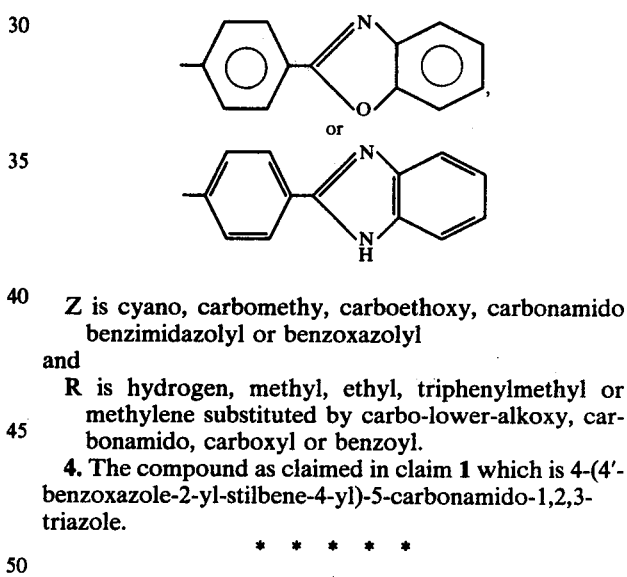

Z is cyano, carbomethy, carboethoxy, carbonamido benzimidazolyl or benzoxazolyl and R is hydrogen, methyl, ethyl, triphenylmethyl or methylene substituted by carbo-lower-alkoxy, carbonamido, carboxyl or benzoyl.

4. The compound as claimed in claim 1 which is 4-(4'-benzoxazole-2-yl-stilbene-4-yl)-5-carbonamido-1,2,3-triazole.

* * * * *